United States Patent
Hakes

(10) Patent No.: US 6,694,830 B2
(45) Date of Patent: Feb. 24, 2004

(54) SAMPLING METHOD AND SAMPLING DEVICE THEREFOR

(76) Inventor: Reggie Hakes, Rte. 1, Box 60, Beaver City, NE (US) 68926

( * ) Notice: Subject to any disclaimer, the term of this patent is extended or adjusted under 35 U.S.C. 154(b) by 11 days.

(21) Appl. No.: 09/899,609

(22) Filed: Jul. 3, 2001

(65) Prior Publication Data

US 2002/0162509 A1 Nov. 7, 2002

Related U.S. Application Data

(60) Provisional application No. 60/273,572, filed on Mar. 3, 2001.

(51) Int. Cl.[7] .............................................. G01N 1/20
(52) U.S. Cl. .............................. 73/863.53; 73/863.54; 73/863.52; 73/863.81; 119/14.14
(58) Field of Search ................... 73/863.51, 863.52, 73/863.53, 863.54, 863.81, 863.82; 119/14.14

(56) References Cited

U.S. PATENT DOCUMENTS

| | | | |
|---|---|---|---|
| 3,600,944 A | * | 8/1971 | Hutchings .................... 73/203 |
| 3,664,306 A | | 5/1972 | Quayle et al. |
| 3,695,230 A | | 10/1972 | Quayle et al. |
| 3,762,371 A | | 10/1973 | Quayle et al. |
| 3,803,921 A | * | 4/1974 | Dieterich ................. 73/863.51 |
| 3,812,722 A | * | 5/1974 | Soudelier ................. 73/863.82 |
| 3,884,187 A | | 5/1975 | Massie et al. |
| 3,968,774 A | | 7/1976 | Massie |
| 4,016,832 A | | 4/1977 | Kiestra |
| 4,199,988 A | * | 4/1980 | Riegger .................... 73/863.51 |
| 4,325,028 A | | 4/1982 | Takahashi |
| 4,346,609 A | * | 8/1982 | Diesel ..................... 73/863.51 |
| 4,385,590 A | | 5/1983 | Mortensen |
| 4,403,568 A | | 9/1983 | Fukuhara et al. |
| 4,442,720 A | * | 4/1984 | Apley et al. ............. 73/863.51 |
| 5,307,696 A | * | 5/1994 | Allain et al. ............. 73/864.74 |
| 5,388,549 A | | 2/1995 | Holroyd |
| 5,572,946 A | | 11/1996 | Holroyd |
| 5,620,008 A | | 4/1997 | Shinar et al. |
| 5,645,012 A | | 7/1997 | Hoefelmayr |
| 5,746,153 A | | 5/1998 | Hoefelmayr |
| 5,829,381 A | | 11/1998 | Nijkamp et al. |

OTHER PUBLICATIONS

Sampling Equipment, Heavy Fuel Oil Drip Sampler, Martechnic, Hamburg, DE http://www.martechnic.de/dripsam-.htm.

Bou–Matic Perfection 3000 Milk Meter, Bou–Matic Corporation, Madison, WI 53708 http://www.bou–matic.com.

* cited by examiner

Primary Examiner—Helen Kwok
Assistant Examiner—Nashmiya Fayyaz
(74) Attorney, Agent, or Firm—Richard L. Marsh

(57) ABSTRACT

An inline sampling device adapted to remove a representative sample drop-wise from a fluid flowing through a fluid line through a sampling probe disposed in the fluid line wherein the sampling probe has at least one fluid receiving, volume relief port adapted for receiving a multiplicity of drop-wise samples of fluid flowing through the fluid line and for discharging a portion of the volume of a sampling container. The device is particularly suitable for testing for mastitis in milking animals.

13 Claims, 3 Drawing Sheets

SAMPLING METHOD AND SAMPLING DEVICE THEREFOR

RELATED APPLICATION INFORMATION

This application is a non-provisional application claiming priority established in provisional patent application No. 60/273,572 filed on Mar. 3, 2001.

BACKGROUND OF THE INVENTION

1. Field of the Invention

This invention relates to a method of sampling a fluid flowing through a line by inserting a sampling device in the line and drop-wise removing a composite sample representative of the quality and quantity of the flow from the line for immediate and/or subsequent analysis.

2. Prior Art Statement

Mastitis is the most costly dairy cattle disease. Without an effective mastitis identification and control program, loss in milk production, discarded or unsalable milk, death or premature culling and decreased genetic advancement can wipe out a dairy farm. Conductivity meters have been used to note a change in an animal's quality as it is believed that the conductivity of the milk from an animal increases with increased mastitis. Somatic Cell Count (SCC) for a herd is effective but costly and lengthy to complete as samples from each animal must be sent to a remote laboratory for testing. An on-site test is the California Mastitis Test which uses a flat paddle with a depression for collecting a sample from each quarter of the mammary. A reagent is applied to each sample to subjectively determine the amount of thickening which is representative of the amount of leukocyte cells present. Some problems with the CMT paddle test for quarters are: loss of the sample from being kicked by the animal, contamination from the environment, slowing of the milking cycle due to the manual nature of the test and finally, the CMT quarter paddle test is not representative of the entire letdown of the animal as somatic cells tend to stratify along with the butterfat over the course of the letdown. Furthermore, testing a large herd consumes a great deal of time.

It has been noted above that electronic samplers are available but generally these meters function too slowly for high-speed milking barns. Furthermore, no sample is retained from most electronic devices to determine the correlation between the multiplicity of meter tests and actual SCC.

It is known to test for the mastitis by provide for conductivity measurements in each quadrant of a milking claw by measuring the conductivity of the milk in a region in the bottom of the claw adjacent the letdown of the individual teat. For instance, see the U.S. Pat. Nos. 3,664,306, 3,695, 230, 3,762,371, issued on May 23, 1972, Oct. 3, 1972 and Oct. 2, 1973, respectively, to Quayle, et al., or the U.S. Pat. No. 4,325,028 issued on Apr. 13, 1982 to Toshio Takahashi, or the U.S. Pat. No. 4,403,568 issued on Sep. 13, 1983 to Fukuhara., et al, or the U.S. Pat. No. 5,829,381 issued on Nov. 3, 1998 to Nijkamp, et al. It is also known to test for mastitis by measuring the conductivity of the milk retained in a spherical chamber disposed in the milk line which receives and retains a portion of the milk flow in a region of the chamber. For instance, see the U.S. Pat. Nos. 3,884,187 and 3,968,774 to Massie issued on Jul. 13, 1976 and Sep. 21, 1973, respectively. Conductivity of the retained portion is measured by electrical probes inserted in the retained portion of the chamber with flow continuing through the retained portion through a drain port disposed in the bottom of the retainer. It is believed that testing at the bottom of the claw only tests the heavier fractions of the milk which is not representative of the entire letdown. It has been found that the above mentioned devices are too slow for high-speed milking operations and require costly sophisticated electronic gear to measure the samples. Furthermore, no sample is retained for correlation with the actual SCC.

Yet further known is a method to extract a sample for determining milk fat content from a milk accumulator in the milking line. The sampling time is dependent upon milk flow as measured by historical data of the animal being milked. A solenoid valve opens and closes based on signals provided by controlling means receiving a flow signal from a separate flow metering device placed before the sampler in the milking line. For instance, see the U.S. Pat. Nos. 5,645,012 and 5,746,153 issued on Jul. 8, 1997 and May 5, 1998, respectively, to Tilman Hoefelnayer. A costly and complicated device with separate electronic controlling means is required to sample by this method. Furthermore, samples are taken at the bottom of the accumulator or the discharge chamber thus sampling only the heavier fractions of milk thus giving a false indication of the total letdown. No test is made for Somatic Cell Count though a sample is retained. The BouMatic volume meter used in the tests below also samples from the bottom of the accumulator.

It is further known to provide a filter in an inline chamber to test the opacity of milk particles accumulated on the filter by optical means as a measure of the amount of mastitis in an individual animal. The milk from each animal is segregated at individual milking stations so an infected animal may be segregated from the herd and treated and the milk retained from admixing with milk from uninfected animals. The entire letdown is measured as the filter accumulates throughout the milking cycle though no sample is removed from the letdown. For instance, see the U.S. Pat. No. 4,385,590 issued on May 31, 1983 to Bruce Mortensen. No sample from the letdown is retained for correlation to actual Somatic Cell Count and the inline filter chamber coupled with the optical means of measuring is costly and complicated.

Additionally, it is known to provide an inline coupler connected by tubing to a pumping unit that continuously draws milk through the tube returning all but timed samples to the milk line. The timed samples are taken approximately every 5 minutes by a cam actuated timer through a two way valve. The inline coupler has a depression in its inner bore at the inlet of the sampling tube to provide a reservoir of milk to be sampled. For instance, see U.S. Pat. Nos. 5,388, 549 and 5,572,946 issued on Feb. 14, 1995 and Nov. 12, 1996, respectively, to Michael Holroyd. It is believed that the reservoir in this device tends to accumulate only the heavier fractions of the milk, thus the samples may not be representative of the flow. It is also believed that samples taken at 5 minute intervals would not be representative of the entire letdown. Holroyd does not retain a sample for correlation.

It is also known to take a drip sample by forcing a portion of fuel into an open container during bunkering a ship. For instance, see www.martechnic.de/dripsam.htm.

Another known milk weighing device accumulates the entire letdown in an accumulator drawing off only air in the accumulator. The accumulator is then agitated by blowing air through a central tube having its end adjacent the bottom of the accumulator. The accumulator is then emptied by drawing the contents of the accumulator through the central tube wherein a sample is taken in a venturi disposed in the vacuum line leading to a storage tank. For instance, see the U.S. Pat. No. 4,016,832 issued on Apr. 12, 1977 to Philippus Kiestra. The sample collector stops sampling when full and would therefore be representative of only part of the letdown. The agitation described in this patent is similar to pouring back and forth between buckets as is proscribed in sample preparation for DHIA testing. It is also believed that since the sampling container is not in the milking line and is not cleaned between the milking of separate animals, cross-contamination of samples is highly possible giving false indications to the herdsman. No disposition of the sample is indicated.

Finally, it is known to provide an inline "T" for positively receiving a sampling tube connector therein. When the sampling tube connector is locked into the "T", one end of a hollow needle punctures a plug in the "T". The other end of the needle has a resealable sheath which may be repeatedly punctured with that end of the needle when sampling tubes are put into the sampling tube connector. Blood pressure of the patient fills the sampling tubes through a single port in the end of the needle. For instance, see the U.S. Pat. No. 5,620,008 issued on Apr. 15, 1997 to Shinar, et al. Though a sample is taken during the blood draw, the tubes fill very quickly and thus are not representative of the entire donation.

SUMMARY OF THE INVENTION

Most sampling devices in the prior art are costly to purchase, operate and maintain. Many require an associated micro or minicomputer to operate. Many of these devices also require the sampling chamber and associated electric measuring probes to be made as a part of the claw or installed in a costly container in the flow line in a milking operation thereby further driving up the cost of installation, operation and maintenance. Therefore, it is an object of this invention to provide an inline sampling device adapted to remove a representative sample drop-wise from a fluid line wherein a sampling probe having at least two fluid receiving, volume relief ports is movably disposed in the fluid line.

It is a further object of this invention to provide an inline sampling device having a sampling probe with at least one fluid receiving, volume relief port movably disposed therein wherein at least one fluid receiving, volume relief port is directed toward the incoming flow.

An additional object of this invention is to provide a sampling device and method of sampling which has a higher correlation of California Mastitis Test (CMT) results with actual Somatic Cell Count (SCC) from the entire letdown of a milked animal than the CMT average of all four quarters to actual SCC level of the individual animal.

Still another object of this invention is to provide an inline sampling device adapted to remove a representative sample drop-wise from a fluid flowing through a fluid line, the inline sampling device comprising a body, a sampling probe and a sampling container wherein the body has an inlet, an outlet with the sampling probe having at least two fluid receiving, volume relief ports movably disposed in the body between the inlet and the outlet.

Another feature of this invention is to provide an inline sampling device comprising a body, a sampling probe and a sampling container wherein the sampling probe has at least one fluid receiving, volume relief port directed toward the incoming flow of the fluid flowing through the fluid line.

Significant to this invention is providing an inline sampling device comprising a body, a sampling probe and a sampling container wherein the sampling probe has a first fluid receiving, volume relief port disposed remote from a lower inside surface of the fluid line and at least a second fluid receiving, volume relief port disposed remote from the first fluid receiving, volume relief port and wherein the second fluid receiving, volume relief port may be disposed above a central axis of the fluid line.

Another important feature of this invention is to provide an inline sampling device comprising a sampling probe having at least one fluid receiving, volume relief port adapted to remove a portion of the volume of the sampling container equal in volume to each drop of fluid received in the sampling container through the at least one fluid receiving, volume relief port.

A valued feature of this invention is to provide an inline sampling device comprising a sampling probe having at least two fluid receiving, volume relief port wherein one of the fluid receiving, volume relief port is adapted to sample heavier molecular weight fractions of the fluid flowing through the fluid line and wherein at least one other fluid receiving, volume relief port is adapted to sample lighter molecular weight fractions of the fluid flowing through line.

Another important object of this invention is to provide an inline sampling device comprising a sampling probe having at least one fluid receiving, volume relief port wherein the sampling probe has one said fluid receiving, volume relief port disposed adjacent a lower inside surface of the fluid line and at least one other fluid receiving, volume relief port disposed remote from the one fluid receiving, volume relief port.

Yet still important to this invention is to provide an inline sampling device having a sampling container removably affixed to the sampling device wherein the sampling container is a standard milk sampling vial snap-fitted in a retaining groove disposed in the body of the sampling device and wherein the retaining groove is concentric with the sampling probe, matches upper lip of sampling vial thereby sealed the sampling vial to the body in the retaining groove. The cap for the sampling vial may be received over a boss on an exterior surface of the body.

Yet another object of this invention is to provide an inline sampling device comprising a body, a sampling probe and a sampling container, the sampling device adapted to remove a representative sample drop-wise from a fluid flowing through a fluid line wherein the body has an inlet, an outlet with the sampling probe fixedly disposed therein between the inlet and the outlet and wherein the sampling probe has at least one fluid receiving, volume relief port adapted for receiving a multiplicity of drop-wise samples of fluid flowing through the fluid line and for discharging a portion of the volume of sampling container into the fluid line in exchange for each drop-wise sample received in the sampling container.

It is an important to dairymen that a feature of this invention is to provide a method of sampling a fluid, such as milk, flowing through a fluid collection line wherein the fluid comprises a stratified fluid wherein at least one layer of higher molecular weight fractions is disposed below at least one layer of lower molecular weight fractions, the method comprises the steps of installing a sampling device in the fluid line, receiving representative samples of the fluid through a sampling probe disposed in a body of the sampling device and accumulating the representative samples throughout the duration of the flow through the line, such as throughout the entire letdown of a milking animal, in a standard sampling vial associated with the sampling device and wherein the method further comprises the step of sampling from at least one layer of higher molecular weight fractions and from at least one layer of lower molecular weight fractions.

It is also important that the method of sampling of this invention provides a sampling probe extending into a fluid flowing through a fluid line, the probe having at least two fluid receiving, volume relief ports disposed in a sidewall thereof that are spaced along the length of the sampling probe wherein the method comprises the step of sampling a stratified flow in the fluid line from at least one layer of higher molecular weight fractions with one fluid receiving, volume relief port and sampling from at least one layer of lower molecular weight fractions with another fluid receiving, volume relief port.

It is particularly advantageous to dairymen that a method of sampling from a fluid, such as milk, flowing through a fluid line provide for moving a sampling probe within a body of sampling device disposed in the milking line between the claw and pipeline connection wherein the method comprises the step of moving at least one fluid receiving, volume relief port disposed in the sampling probe into a different layer of higher molecular weight fractions of the fluid flow and moving another fluid receiving, volume relief port into a different layer of lower molecular weight fractions of to accommodate for different levels of fluid flow.

DESCRIPTION OF THE PREFERRED EMBODIMENTS

While the various features of this invention are hereinafter described and illustrated as an inline sampling device adapted to remove a representative sample drop-wise from a fluid line wherein the sampling device comprises a sampling probe having a fluid receiving, volume relief port disposed in a through passage of the sampling device, the sampling probe removably disposed in the inline sampling device, it is to be understood that the various features of this invention can be used singly or in various combinations thereof to remove a representative sample from a fluid line for immediate or subsequent testing as can hereinafter be appreciated from a reading of the following description.

Figure 1:
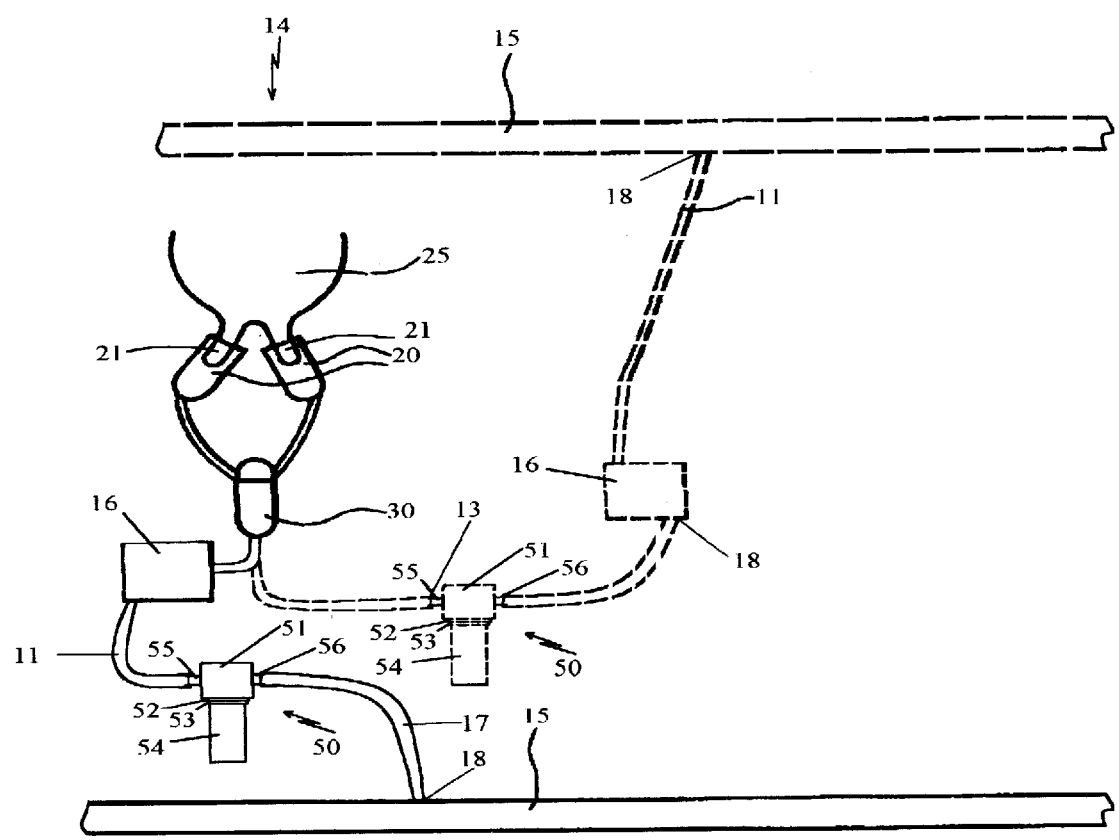
FIG. 1 is an elevation view of a milking system showing the preferred embodiment of the inline sampling device of this invention shown installed in the milking line after the milking meter and an alternate arrangement with the inline sampling device installed in the milking line before the meter.
Figure 2:
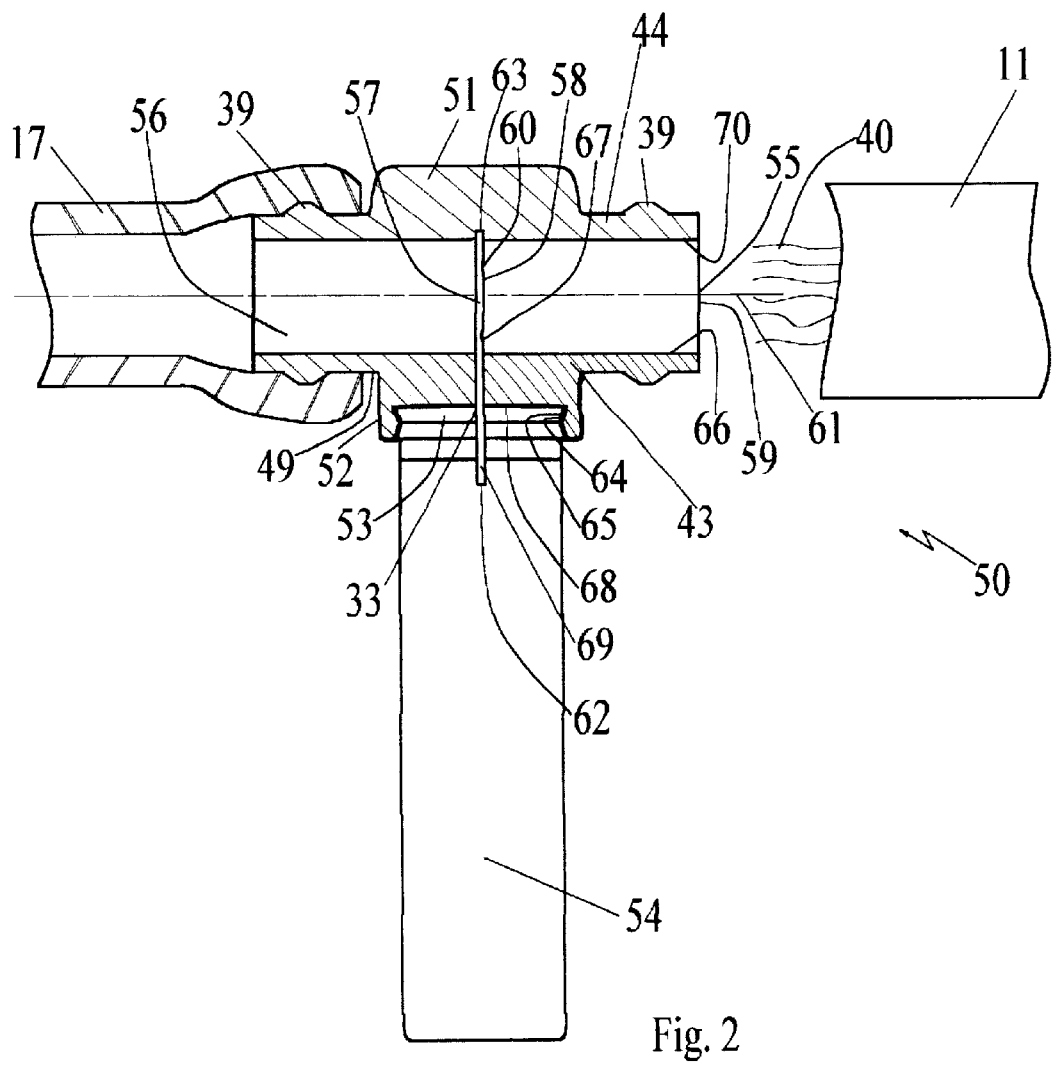
FIG. 2 is a enlarged plan view of the preferred embodiment of the inline sampling device of this invention with body and connected hose in cross section to show internal features.

Referring now to FIGS. 1 and 2, an inline sampling device, generally referred to by the numeral 50 is adapted to remove a representative sample drop-wise from a fluid flowing through a fluid line 11. Sampling device 50 comprises a body 51, a sampling probe 57 and a sampling container or vial 54, body 51 having an inlet 55, an outlet 56 and a sampling container or vial receiving boss 52, vial receiving boss 52 having a recess 53 disposed therein for sealingly receiving a mating lip 65 of vial 54 therein. Sampling probe 57 is disposed in body 51 between inlet 55 and outlet 56, inlet 55 communicating with outlet 56 in a through fluid passage 59 passing through body 51. Sampling probe 57 has at least two fluid receiving, volume relief ports 60, 67 wherein sampling probe 57 may be movably disposed in body 51 as will be hereinafter fully explained. Inline sampling device 50 is most suitable for sampling the letdown of each milk cow of a herd to monitor the health of the herd and specifically to monitor each animal for mastitis though inline sampling device 50 may be used for drawing samples from any fluid line 11 wherein fluid line 11 may be broken at a point 13 along the length thereof. Though inline sampler 50 is described herein as particularly useful for mastitis testing of milking herds by removing a sample from the vacuum operated fluid line 11 wherein the entire system is under a vacuum, it should be readily appreciated that inline sampler 50 could as easily be inserted in a fluid line 11 carrying fluids under pressure. For instance, it is contemplated that inline sampler 50 might be used to sample blood throughout a donation, fluids pumped from a truck to a storage tank or from a storage tank to a mobile vehicle or throughout a chemical process plant where it becomes desirable to ascertain the state of the chemical process at various stages.

In a milking system, generally referred to by the numeral 10, fluid line 11 is the connecting line between a milking collection container or claw 30 and the receiving line 15, wherein receiving line 15 is connected to each milking station 14 throughout the milking barn. Only one milking station 14 is shown in FIG. 1, however, those skilled in the art will appreciate that milking stations 14 are arranged in close proximity and may further be arranged in parallel rows wherein collection line 15 services adjacent rows. In some milking barns, collection line 15 is situated above the milking floor as shown in dashed lines wherein sampling device 50 is shown between the claw 30 and the milk volume meter 16 though in the preferred embodiment described herein, milk collection line 15 is arranged below the milking floor and inline sampling device 50 is disposed in fluid line 11 between milk volume meter 16 and collection line 15. Though the preferred embodiment is shown as connected in a "double 25 parallel" milking parlor, it should be understood here that inline sampling device 50 may be used in any size milking parlor with any number of milking machines with the same results noted in this invention. For instance, inline sampler 50 has also been successfully used in rotary/carousel, standard, subway, high-line stanchion, flat barn and swing parlors.

In a milking parlor, fluid line 11 is generally a one inch outside diameter, five-eighths inch inside diameter sanitary food grade polymeric tubing and thus fluid line 11 may easily be broken at any point 13 along the length thereof by cutting with a sharp knife. As inline sampling device 50 is preferably situated either closely adjacent to milking meter 16 or fluid collecting line 15, point 13 may be made approximately 3 inches from either milking meter 16 or fluid collection line 15 wherein the three inch length of tubing is adapted to remain with inline sampling device 50 when inline sampling device 50 is removed from the milking parlor when a particular round of sampling is finished. While placed in fluid line 11, inline sampling device 50 is cleaned in the normal cleaning and rinsing cycle between the milking of one animal and the next animal at a particular milking station 14. When removed from the milking parlor after testing is completed for a particular round, inline sampling device 50 is thoroughly washed, rinsed, sterilized and stored in a sterile environment awaiting use for the next round of sampling of the herd. Preferably, each milking station 14 has an inline sampling device 50 associated therewith. It should be apparent here that inline sampling device 50 is used periodically to monitor the health of the herd by placing inline sampling device 50 in each milking line approximately once each month though sampling may be done at different intervals based on herd history and or unusual environmental conditions. Thus, fluid line 11 need be cut at point 13 only once and thereafter inline sampler 50 affixed to either collection line 15 or milking meter 16 when sampling is desired. As shown in the preferred embodiment in solid lines in FIG. 1, point 13 of fluid line 11 is removed from collection line 15 and removably affixed to inlet end 55 while short section 17 of fluid line 11 is removably affixed to outlet end 56 of inline sampler 50 and is connected to collection line 15 along with inline sampler 50. When sampling is no longer needed., short section 17 of fluid line 11 is removed along with inline sampler 50 from collection line 15 and point 13 is re-attached to collection line 15. In this manner, milking without sampling may proceed. Of course, when inline sampler 50 is removably affixed between claw 30 and milking meter 16 short section 17 of fluid line 11 may be taken from fluid line 11 between claw 30 and milking meter 16 or merely cut from a spare length of fluid line 11 and removably affixed to inline sampler 50. Thus, it should be readily apparent that inline sampler may be placed anywhere in fluid line 11, and removably affixed to a connection point 18 within fluid system 10 having at least one fluid receiving, volume relief port 60, 67 directed toward the incoming flow of fluid 40 flowing through fluid line 11 wherein fluid 40 passes through fluid passage 59 from inlet 55 toward outlet 56. It is not necessary to remove any equipment installed in fluid line 11 in order to install inline sampler 50 and in fact, inline sampler 50 may be installed in existing fluid lines to augment other testing devices of the prior art and/or to provide a cross correlation with those testing devices.

Referring specifically to FIG. 2, inline sampling device 50 preferably has sampling probe 57 disposed within body 51 wherein one fluid receiving, volume relief port 67 is disposed remote from a lower inside surface 66 of a fluid passage 59 through body 51 from inlet 55 to outlet 56 and at least one other fluid receiving, volume relief port 60 disposed remote from the one fluid receiving, volume relief port 67, fluid passage 59 receiving flow of fluid 40 from fluid line 11. Fluid receiving volume relief ports 60, 67 are small diameter orifices provided into sidewall 58 of sampling probe 57 and are oriented to face incoming fluid 40. Typically, fluid receiving, volume relief ports 60, 67 are from about 0.005 to about 0.020 inch in diameter though different diameters may be provided based on the viscosity of fluid 40 being sampled. As shown in FIG. 2, preferably sampling device 50 has the at least one other fluid receiving, volume relief port 60 disposed above a central axis 61 of fluid passage 59 and hence, in this installation, also a corresponding central axis of fluid line 11. Though inline sampler 50 is shown and described as being installed in fluid line 11, inline sampler may be directly connected to another device in system 10 without short section of line 17 by manufacturing at least one of ends 55, 56 with another connection such as a threaded connector. Furthermore, inline sampler 50 is generally installed such that central axis 61 aligns with a corresponding central axis in fluid line 11, however, either or both ends 55, 56 may be made with an angled connection without departing from the scope of this invention.

Still referring to FIG. 2, inline sampling device 50 functions by removing a portion of the volume of sampling vial 54 equal in volume to each drop of fluid received in sampling vial 54 through fluid receiving, volume relief ports 60, 67 as drop-wise sampling of fluid 40 and removal of volume alternate, fluid receiving, volume relief ports 60, 67 discharging a portion of the volume of sampling vial 54 into fluid line 11 in exchange for each drop-wise sample received in sampling vial 54. Specifically, in a fluid system 10 such as a milking parlor, vacuum is supplied to collection line 15 to move fluid 40 from each teat 21 of under 25 of an animal into collection cups or claws 30 to a storage tank within system 10. The entire operation of a milking system is not repeated here as it is well known in the art. The vacuum supplied to collection line 15 also places any installed equipment within system 10 between teat cups 20 and collection line 15 under substantially the same vacuum. Thus, inline sampler 50 is placed under vacuum and as vial 54 is sealingly affixed to body 51 at sealing surface 68 disposed adjacent retaining groove 64, sealing surface 68 sealing against an open top of vial 54 wherein vial 54 is removably affixed to body 51 by mating lip 65 fitted into retaining groove 64. As vial 54 is placed under vacuum at the beginning of a milking operation, a small volume of vial 54 is removed prior to the arrival of any fluid 40 at sampling probe 57 and thus when fluid 40 arrives at sampling probe 57, drop-wise samples of fluid 40 are deposited in vial 54 and the partial pressure within vial 54 is raised above the vacuum of system 10. Thus, upon depositing each drop of fluid 40 in vial 54 through open end 62 of sampling probe 57, a corresponding volume is removed from vial 54 through open end 62, bore 69 of sampling probe 57 and into fluid passage 59 of body 51. This process repeats throughout the time that fluid 40 flows through system 10 until fluid 40 ceases to flow and/or vacuum is removed from system 10. As fluid 40 tends to stratify within fluid line 11 and hence within fluid passage 59 of body 51, heavier molecular weight fractions would tend to move along lower inside surface 66 of fluid passage 59 and hence one fluid receiving, volume relief port 67 is adapted to sample these heavier molecular weight fractions and at least one other fluid receiving, volume relief port 60 is adapted to sample lighter molecular weight fractions of fluid 40 flowing through said fluid line 11. Specifically, sampling probe 57 has one fluid receiving, volume relief port 67 disposed adjacent a lower inside surface 66 of fluid passage 59 thus sampling heavier weight fractions flowing through fluid line 11 and another fluid receiving, volume relief port 60 disposed remote from one fluid receiving, volume relief port 67. Drops of fluid sampled through sampling probe 57 pass into vial 54 through open end 62 of sampling probe 57, the entrained equal volume also passing through open end 62 of sampling probe 57. The entrained equal volume of vial 54 is admitted to fluid line 11 and carried away from sampling probe 57 in between drops admitted to vial 54, the entrained equal volume leaving thereby creating space for a new droplet from sampling probe 57. As flow 40 through fluid line 11 varies throughout a milking cycle, some drop-wise sampling may occur only through lower fluid receiving, volume relief port 67 while commonly both fluid receiving, volume relief ports 60, 67 are receiving drop-wise samples therethrough. Furthermore, it is important to continue sampling throughout the entire letdown of the milking cycle as somatic cells also tend to stratify from the beginning of the letdown to the end thereof and samples throughout the entire letdown captures the most representative sample of the animal. Vial 54 may then be used to complete a California Mastitis Test (CMT) for the entire letdown by spreading a small sample on the CMT paddle and treating the small sample with the reagent. The remainder of the sample may be retained to test for conductivity or send to a remote laboratory for actual Somatic Cell Count (SCC). Thus, cross-correlation may be established between the composite CMT and the actual SCC. Since an indication of the health of an animal may be determined substantially immediately after the milking of that animal by the composite CMT test, animals with higher CMT scores may be separated from the herd and treated with these animals preferably also placed in a separate milking string and milked after lower CMT score animals. The milk from the different strings may then be separated and sold at higher quality levels and hence more profit for low SCC milk. This practice will reduce the possibility of spreading mastitis pathogens to uninfected animals during milking. Sampling of all animals in the herd is easily accomplished with inline sampling device 50 as each sampling vial 54 is removably affixed to sampling device 50 and is removed therefrom after completion of the milking cycle for each animal. Specifically, sampling vial 54 of sampling device 50 is a standard hinged top milk sampling vial, made by method described in U.S. Pat. No. 4,783,056 incorporated herein by this reference thereto, vial 54 snap-fitted in retaining groove 64 disposed in body 51 of sampling device 50 wherein groove 64 is preferably concentric with sampling probe 57.

The method of sampling a fluid 40 flowing through a fluid line 11 comprises the steps of installing sampling device 50 in fluid line 11, receiving representative samples of fluid 40 through sampling probe 57 disposed in body 51 of sampling device 50 and accumulating the representative samples in sampling vial 54 associated with sampling device 50 for immediate and subsequent testing for clinical and subclinical pathogens and for a representative quantity measurement. The method of sampling fluid 40 flowing through fluid line 11 is most important when fluid 40 comprises a stratified fluid wherein at least one layer of higher molecular weight fractions is disposed below at least one layer of lower molecular weight fractions. Thus, the method of this invention further comprises the step of sampling from at least one layer of higher molecular weight fractions and from at least one layer of said lower molecular weight fractions by disposing sampling probe 57 with at least two fluid receiving, volume relief port 60, 67 disposed in a sidewall 58 thereof, wherein fluid receiving, volume relief ports 60, 67 are spaced along the length of sampling probe 57, the one layer of higher molecular weight fractions sampled with fluid receiving, volume relief port 67 and the one layer of lower molecular weight fractions sampled with another said fluid receiving, volume relief port 60. Though not entirely necessary, it has been found by the teachings of this invention that the method of sampling is best achieved wherein at least one fluid receiving, volume relief port 60 disposed in the one layer of higher molecular weight fractions, and preferably all, but at least also fluid receiving, volume relief port 67 disposed in the one layer of lower molecular weight fractions is directed toward the incoming flow of fluid 40 flowing through fluid line 11. The inventor hereof has utilized the method and apparatus of this invention to control mammary disease in his own herd, however, felt it important to have at least one independent blind study done to further verify findings in his own herd. Thus, a test was conducted by the Dairy Herd Improvement Association (DHIA) of California, wherein two different milking strings were tested using the method and apparatus of this invention. The test involved installing inline sampler 50 before a BouMatic volume measuring meter in the milking line of fluid system 10 and collecting the output of each animal in a bucket. A large sample was taken by the BouMatic and inline sampler 50 removed a representative sample throughout the entire letdown with the milk from each letdown subsequently tested for Somatic Cell Count. Standard sampling techniques were used for sampling from each of the buckets of milk from which two control samples Control A and Control B were drawn. Three separate tests were conducted on 74, 94 and 167 animals with comparisons drawn between inline sampler 50, the BouMatic Meter and laboratory SCC. These results are reproduced below in Table 1 with all comparisons made to control B.

TABLE 1

| | Somatic Cell Count as compared to Control B | | |
|---|---|---|---|
| | Inline Sampler | BouMatic | Control A |
| n = 74 | | | |
| Average Difference | 7 | 2 | −55 |
| Std. Deviation | 70 | 82 | 172 |
| n = 94 | | | |
| Average Difference | 11 | 0 | −40 |
| Std. Deviation | 88 | 76 | 114 |
| n = 167 | | | |
| Average Difference | 5 | 0 | −53 |
| Std. Deviation | 69 | 62 | 136 |

It can be readily observed that inline sampler 50 of this invention compares most favorably with samples taken by the much more expensive BouMatic meter and is significantly superior to standard sampling techniques wherein the fluid collected is poured between two buckets three times for mixing purposes before a dip sample is removed therefrom. Stated another way, the Standard Deviation between control samples above is significantly greater than the Standard Deviation of either inline sampler 50 or the BouMatic meter.

Another test for correlation purposes was conducted with the help of J. C. Gillespie, DVM.MS of Gillespie Veterinary Service, P C, McCook, Nebr., wherein a CMT was performed on each quarter of each animals mammary, a CMT was performed on the entire letdown of each animal according to the teachings of this invention and the samples collected in vial 54 were sent to the Heart of America DHIA for SCC on each identified animal. One hundred animals were selected at random with selection determined by the position in which each individual animal entered the double 25 parallel milking parlor. Correlation was excellent as shown in Table 2 below wherein the CMT score is as follows:

0—no reaction

1—slight increase in thickening of sample

2—obvious change in viscosity of sample

3—heavy thickening of sample

4—visible separation or aggregate in sample

The average of the four quarter CMT test is shown in column 1 adjacent to the CMT derived from the inline sampler 50 while the average SCC is shown in column 3 next to the average CMT.

TABLE 2

| CMT Score Inline Sampler 50 | Four Quarter Average California Standard CMT | Average SCC Laboratory analysis |
|---|---|---|
| 0 | 0.4 | 51,667 |
| 1 | 1.5 | 346,000 |
| 2 | 1.4 | 1,109,158 |
| 3 | 2.0 | 3,802,600 |
| 4 | 1.7 | 4,906,857 |

With the advent of the maximum Bulk Tank SCC of 750,000 for compliance with State and Federal Pasteurized Milk Ordinance, inline sampler 50 readily points out a cause for concern when the CMT score from inline sampler 50 reaches 1, quite significant since CMT from inline sampler 50 may be conducted for less than one cent per animal and can be done within two hours of milking. Thus, inline sampler 50 is highly cost effective for the dairyman in early detection and control of mastitis without the troubles of conducting the four quarter test on each individual animal.

Figure 3:
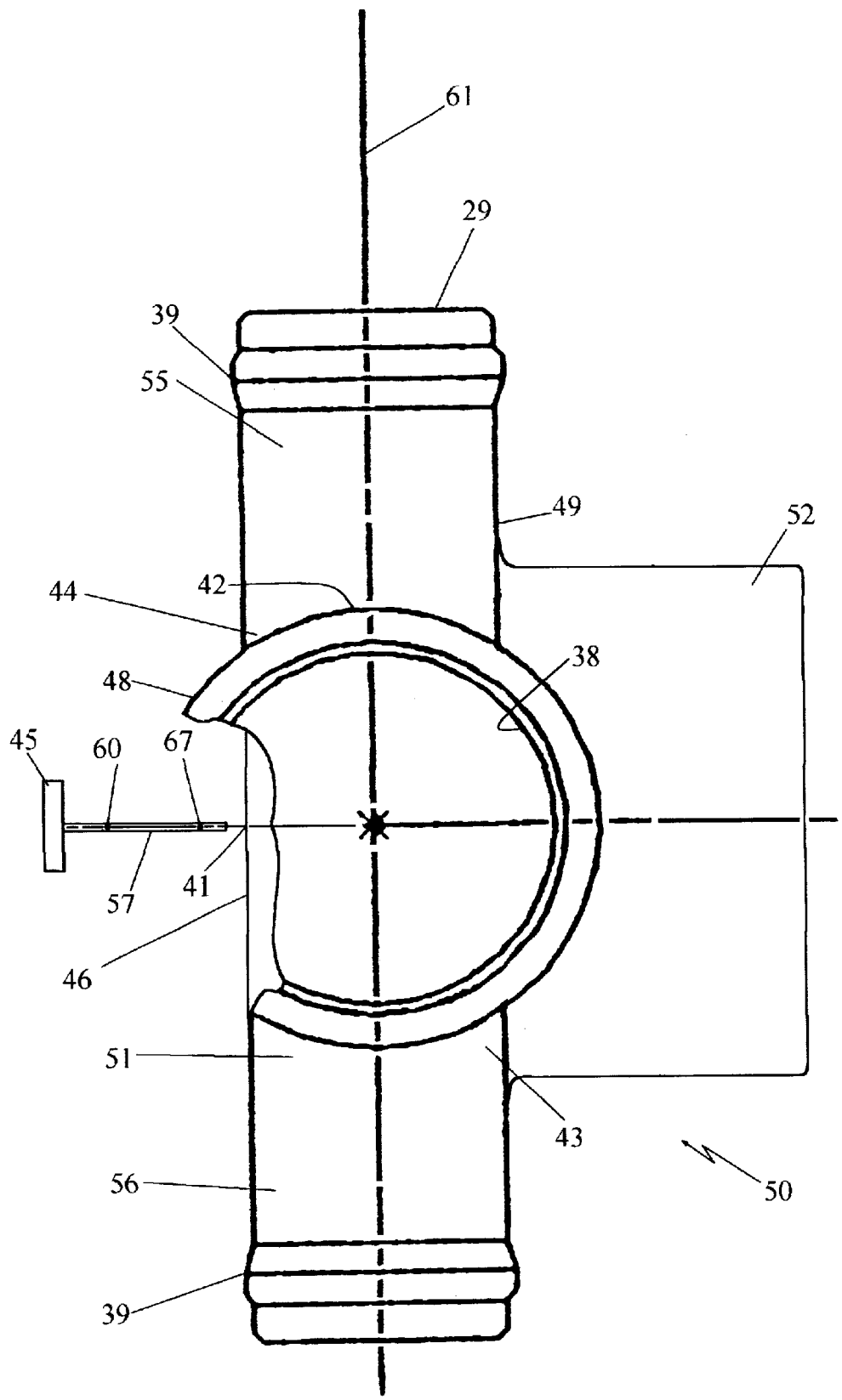
FIG. 3 is a side view of the inline sampling device of this invention showing an adjusting means disposed above a top surface thereof.

Referring now to FIGS. 2 and 3, the method of sampling of this invention also provides for sampling probe 57 to be movable within body 51, wherein the method further comprises the step of moving fluid receiving, volume relief port 67 into a different layer of higher molecular weight fractions and moving fluid receiving, volume relief port 60 into a different layer of lower molecular weight fractions of fluid 40 flowing through fluid flow line 11. Specifically, it may be desired to move fluid receiving, volume relief port 67 from a position adjacent lower inside wall 66 of a fluid passage 59 disposed within body 51 of sampling device 50 to a position approximately midway between lower inside wall 66 of fluid passage 59 and central axis 61 of fluid passage 59. As the preferred embodiment of sampling probe 57 described herein has at least two fluid receiving, volume relief ports, 60, 67 the method of sampling also generally comprises the step of moving fluid receiving, volume relief port 60 from a position substantially at a central axis 61 of a fluid passage 59 disposed within body 51 of sampling device 50 to a position approximately midway between central axis 61 of fluid passage 59 and an upper inside wall 70 of fluid passage 59. Referring now to FIG. 3, it is contemplated within the scope of this invention to provide a bore 41 through upper surface 46 of body 51, bore 41 passing through upper portion 44 and lower portion 43 of body 51 through sealing surface 68. Bore 41 is substantially the same diameter as sampling probe 57 such that sampling probe 57 is sealingly engaged therewith. Sampling probe 57 may have a solid push/pull button 45 on other end 63 of probe 57, wherein probe 57 is fixedly mounted therein and is adapted to be moved through bore 41 by moving push/pull button 45 upwardly away from upper surface 46 or downwardly toward upper surface 46. Sampling probe 57 has open end 62 extending through tight fitting bore 41 into vial 54 for delivering samples thereinto. Sampling probe 57 may alternately be affixed to or made a part of a rack and pinion set wherein the position of fluid receiving, volume relief ports 60, 67 is controlled by a thumb screw affixed to the pinion of the rack and pinion set disposed within body 51. Alternately, a portion of button 45 may be threaded and adapted to be placed in a threaded hole in bore 41 wherein sampling probe 57 may be adjusted upwardly and downwardly by turning button 45 thus moving the thread in the threaded bore. Thus, fluid receiving, volume relief ports 60, 67 may be adjusted during flow of fluid 40 through fluid passage 59 for lower flows or for sampling different strata within a given flow of fluid 40. Preferably, however, fluid receiving, volume relief port 67 is fixed at a distance of approximately 0.110 inch from lower inside surface 66 of fluid passage 59 while fluid receiving, volume relief port 60 is spaced from fluid receiving, volume relief port 67 approximately 0.315 inch thus placing fluid receiving, volume relief port 60 above central axis 61.

Though the preferred embodiment described above and shown in FIGS. 1 and 2 has a single sampling probe 57, it is entirely within the scope of this invention to provide at least one other sampling probe 57 extending into and/or through fluid passage 59 to provide for sampling of fluid 40 flowing through fluid passage 59 by providing at least one fluid receiving, volume relief port 60, 67 in each sampling probe 57. It is also within the scope of this invention to offset at least one sampling probe 57 relative to center 33 of sealing groove 64 for instance wherein fluid passage 59 has an elongated bottom surface 66 as in a square fluid passage 59. Where multiple sampling probes 57 are provided, it is usually the practice to arrange the multiple probes in spaced apart fashion transverse the direction of flow though of course, the multiple probes may be arranged in linear fashion in the direction of flow. Where multiple probes are used, one fluid receiving, volume relief port 67 may be arranged such that it is directed toward the direction of flow of fluid 40, that is upstream while another fluid receiving, volume relief port 60 is directed away from the flow of fluid 40, that is downstream. It is also possible to provide for one sampling probe 57 to be offset upstream relative to center 33 along axis 61 of fluid passage 59 with fluid receiving, volume relief port 67 directed into the flow of fluid 40 while another sampling probe 57 is offset downstream relative to center 33 along axis 61 wherein fluid receiving, volume relief port 60 is directed downstream. Thus, fluid receiving, volume relief port 67 receives drop-wise samples of fluid from fluid 40 in the one probe 57 while fluid receiving, volume relief port 60 provides for volume relief of vial 54 in the other probe 57.

Also shown in FIG. 3 is a cap receiving boss 48 on surface 42 adapted for receiving the cap of a hinged top, standard milk sampling vial thereon and thus the cap of vial 54 may be kept clean during the sampling of fluid line 11. Though shown only on side 42 of body 51, it is also possible to have cap receiving boss 48 disposed on a side opposite side 42.

In one alternate embodiment for use in a pressure line, it has been found that two probes arranged in sequential fashion along the direction of flow through fluid line 11 provides for drop-wise sampling of fluids under pressure. In this arrangement one fluid receiving, volume relief port 67 is directed upstream toward the direction of flow of fluid 40 while another fluid receiving, volume relief port 60 is directed downstream. With fluid receiving, volume relief port 60 is directed downstream, flow of fluid 40 through fluid line 11 tends to slightly reduce the pressure at fluid receiving, volume relief port 60 while fluid receiving, volume relief port 67 directed upstream tends to provide a small pressure against fluid receiving, volume relief port 67 wherein the slight pressure against port 67 and the slight reduction of pressure adjacent port 60 provides for drop-wise entry of fluid 40 from fluid line 11 into vial 54 and removal of volume from vial 54 back into fluid line 11. In this alternate embodiment, vial 54 generally has a threaded connection as mating lip 65 and body 51 has a corresponding threaded connection for sealingly sealing vial 54 against sealing surface 68. It may also be possible to use inline sampler 50 to connect directly to a device for testing of fluid 40 from fluid line 11 wherein drop-wise samples are passed directly into the testing device by connecting open end 62 to a sampling tube also connected to the testing device. In the blood sampler described in the aforementioned U.S. Pat. No. 5,620,008 to Shinar, et al., the needle probe of Shinar, et al., would be replaced by two separate needles each puncturing the plug in the "T" shaped connector and the seal on the blood sampling vial wherein at least one fluid receiving, volume relief port 67 would be directed upstream into the outflow of blood while another fluid receiving, volume relief port 60 would be directed downstream away from the outflow of blood thus providing for the drop-wise sampling of blood throughout the blood donation. Of particular use, this alternate embodiment would be installed in an inlet line to a milk storage tank for receiving milk from a bulk tank truck wherein drop-wise sampling could be conducted over the course of the unloading thereby eliminating the errors inherent in dip cup sampling of the entire tank load as the tank has a tendency to stratify from top to bottom. It should be readily apparent here that drop-wise sampling during unloading would give an overall measure of the quality of the bulk truck tank load and thus give both the dairyman and the dairy the best value for the load. In this case, not only Somatic Cell Count testing can be conducted but butter fat, protein, lactose, solids-not-fat and Milk Urea Nitrogen contents can all be determined from the drop-wise sample.

In yet another embodiment, sampling probe 57 may comprise a sharpened hollow needle which is directly inserted into fluid line 11 wherein other end 63 is a closed sharp point and open end 62 is open to an internal bore within the hollow needle. Fluid receiving, volume relief ports 60, 67 would be disposed into sidewall 58 of this sampling probe 57 and situated in fluid line 11 by moving sampling probe 57 inwardly or outwardly by hand. Sample vial 54 would then be sealingly affixed to open end 62 directly, have a cap with a puncturable seal, have a sampling tube connected thereto directly into a sampling device or be attached to a body similar to body 51 wherein having only bore 41 passing therethrough to be sealingly sealed to sample vial 54. This alternate would be useful in milking barns wherein the milking line is an elastomeric tube which is easily punctured with a sharp needle point.

In a method of making inline sampler 50 prototypes were machined from a 2 inch square, 3½ inch long solid block of Ultra High Molecular Weight Polyethylene (UHMW) by disposing a bore 29 through body 51 thereby establishing fluid passage 59. Thereafter, inlet 55 and outlet 56 were turned from the solid block of UHMW, each of inlet 55 and 56 extending equally and oppositely from a 1¾ inch square main portion of body 51. At least one hose sealing barb 39 is disposed on each of inlet 55, 56 for retaining fluid line 11 upon these extensions of inline sampler 50. Inlet 55 and outlet 56 are typically larger than the inside diameter of fluid line 11 as fluid line 11 is adapted to be force fitted thereover. In this preferred embodiment, inlet 55 and outlet 56 have an outside diameter of 0.840 inch while barb 39 is typically 0.900 inch in diameter. Though fluid line 11 is typically only ⅝ inch inside diameter, since it has no reinforcement therein, it may easily be stretched over inlet 55 or outlet 56 and retained thereon by barb 39 as fluid line 11 will recover some of its original diameter to rest against 0.840 inch dimension of inlet 55 or outlet 56. Cap bosses 48 were provided on both side edges 42 by machining a circular boss from the main portion of body 51 wherein a ridge 38 is provided to receive a mating portion of the cap of vial 54. Vial receiving boss 52 was then machined into lower surface 49 of body 51, vial receiving boss 52 having sealing surface 68 adjacent lip receiving groove 64. Lip receiving groove 64 is undercut into vial receiving boss 52 and is adapted to have lip 65 of vial 54 snap-fitted therein. Lip receiving groove 64 mates solidly with lip 65 of vial 54 such that vial 54 is sealing engaged with sealing surface 68 inside of vial receiving boss 52. Finally, bore 41 is provided through sealing surface 68, lower portion 43 and into upper portion 44 of body 51 wherein other end 63 of sampling probe 57 is disposed. Bore 41 is typically 0.065 inch in diameter such that sampling probe 57 tightly fits therewithin and is sealingly engaged in the portion of bore 41 disposed in upper portion 44 of body 51. A stainless steel tube 0.065 in outside diameter and 0.050 inside diameter is cut to a length of 1.200 inches and has fluid receiving, volume relief port 67 drilled through sidewall 58 at a distance of 0.570 from open end 62 and further has fluid receiving, volume relief port 60 also drilled through sidewall 58 at a distance of 0.325 from fluid receiving, volume relief port 67, fluid receiving, volume relief port 60 disposed closest to other end 63 thus establishing sampling probe 57. Other end 63 may be sealed by pinching the end thereof, but it has been found that as other end 63 is sealing engaged with bore 41 in upper portion 44 of body 51, it is unnecessary to close other end 63. Once sampling probe 57 is created, other end 63 thereof is inserted into bore 41 from sealing surface 68 and forced upwardly through body 51 into upper portion 44 thereof wherein other end 63 extends into upper portion 44 and open end 62 extends just below sealing surface 68. A short section 17 of milking line is then forced over a sealing barb 39 on outlet end 56 readying inline sampler 50 for use in sampling fluid 40 from fluid line 11. Though prototypes of inline sampler 50 were machined from UHMW solid material, inline sampler 50 may also be molded of Type I, II, III or IV engineered thermoplastics previously certified for use in food grade applications. Preferably, inline sampler 50 will be injection molded of Delrin®, a registered trademark of DuPont for an acetal resin though other Type I, II, III or IV plastics may also be used. Furthermore, inline sampler 50 may be machined from stainless steel or fabricated from stainless steel parts without departing from the scope of this invention.

While the present invention has been described with reference to the above described preferred embodiments and alternate embodiments, it should be noted that various other embodiments and modifications may be made without departing from the spirit of the invention. Therefore, the embodiments described herein and the drawings appended hereto are merely illustrative of the features of the invention and should not be construed to be the only variants thereof nor limited thereto.

I claim:

1. An inline sampling device adapted to remove a representative sample drop-wise from a fluid flowing through a fluid line, said sampling device comprising a body, a sampling probe and a sampling container, said body having an inlet, an outlet, said sampling probe disposed in said body between said inlet and said outlet, said sampling probe having at least two fluid receiving, volume relief ports wherein each said drop-wise sample of said fluid is received in said sampling container through at least one of said fluid receiving, volume relief ports, said each drop-wise sample of said fluid displacing an equal volume portion of the volume of said sampling container, said equal volume portion of said volume alternately discharged into said fluid line through at least one of said fluid receiving, volume relief ports wherein said sampling probe has one of said fluid receiving, volume relief ports disposed adjacent a lower inside surface of a bore passing through said body from said inlet to said outlet and another of said fluid receiving, volume relief ports disposed remote from said one fluid receiving, volume relief port, said one fluid receiving, volume relief port adapted to sample heavier molecular weight fractions of said fluid flowing through said fluid line.

2. An inline sampling device as in claim 1 wherein said sampling probe has said one fluid receiving, volume relief port directed toward said fluid flowing through said fluid line.

3. An inline sampling device as in claim 1 wherein said another fluid receiving, volume relief port is disposed below a central axis of said bore.

4. An inline sampling device as in claim 1 wherein said sampling probe is movably disposed in said body.

5. An inline sampling device as in claim 1 wherein accumulation of drop-wise samples received in said container provides a measure of the total quantity of said heavier weight fractions of said fluid flowing through said fluid line.

6. An inline sampling device as in claim 1 wherein said sampling container is removably affixed to said sampling device.

7. An inline sampling device as in claim 6 wherein said sampling device has a standard milk sampling vial snap-fitted in a retaining groove disposed in said body of said sampling device.

8. An inline sampling device as in claim 7 wherein said groove is concentric with said sampling probe.

9. An inline sampling device adapted to remove a representative sample drop-wise from a fluid flowing through a fluid line, said sampling device comprising a body, a sampling probe and a sampling container, said body having an inlet, an outlet, said sampling probe disposed in said body between said inlet and said outlet, said sampling probe having at least two fluid receiving, volume relief ports wherein each said drop-wise sample of said fluid is received in said sampling container through at least one of said fluid receiving, volume relief ports, said each drop-wise sample of said fluid displacing an equal volume portion of the volume of said sampling container, said equal volume portion of said volume alternately discharged into said fluid line through at least one of said fluid receiving, volume relief ports wherein said sampling probe has one of said fluid receiving, volume relief ports disposed adjacent a lower inside surface of a bore passing through said body from said inlet to said outlet and another of said fluid receiving, volume relief ports disposed remote from said one fluid receiving, volume relief port, said another fluid receiving, volume relief port adapted to sample lighter molecular weight fractions of said fluid flowing through said fluid line.

10. An inline sampling device as in claim 9 wherein said sampling probe has said another fluid receiving, volume relief port directed toward said fluid flowing through said fluid line.

11. An inline sampling device as in claim 9 wherein accumulation of drop-wise samples received in said container provides a measure of the total quantity of said lighter weight fractions of said fluid flowing through said fluid line.

12. An inline sampling device as in claim 9 wherein said sampling probe is movably disposed in said body.

13. An inline sampling device as in claim 9 wherein said one fluid receiving, volume relief port is disposed above a central axis of said bore.

* * * * *